US012161548B2

(12) United States Patent
Sussman et al.

(10) Patent No.: US 12,161,548 B2
(45) Date of Patent: *Dec. 10, 2024

(54) INTRAOCULAR DRUG DELIVERY PLATFORM

(71) Applicants: SpyGlass Pharma, Inc., Aliso Viejo, CA (US); The Regents of the University of Colorado, a body corporate, Denver, CO (US)

(72) Inventors: Glenn Robert Sussman, Aliso Viejo, CA (US); Craig Alan Cable, II, Aliso Viejo, CA (US); Malik Y. Kahook, Denver, CO (US)

(73) Assignees: SpyGlass Pharma, Inc., Aliso Viejo, CA (US); The Regents of the University of Colorado, a body corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/485,546

(22) Filed: Oct. 12, 2023

(65) Prior Publication Data

US 2024/0074848 A1 Mar. 7, 2024

Related U.S. Application Data

(63) Continuation of application No. 17/183,985, filed on Feb. 24, 2021, now Pat. No. 11,813,159.

(Continued)

(51) Int. Cl.
*A61F 2/16* (2006.01)
(52) U.S. Cl.
CPC .......... *A61F 2/16* (2013.01); *A61F 2002/169* (2015.04); *A61F 2002/16901* (2015.04);
(Continued)

(58) Field of Classification Search
CPC ............ A61F 9/0017; A61F 2250/0067; A61F 2250/0068; B29D 11/00096
See application file for complete search history.

(56) References Cited

U.S. PATENT DOCUMENTS 6,986,900 B2 * 1/2006 Yaacobi .................. A61P 37/06
424/427
7,713,299 B2 5/2010 Brady et al.
(Continued)

FOREIGN PATENT DOCUMENTS

| EP | 1653886 B1 | 1/2008 |
|----|-----------|--------|
| WO | 2008094518 A1 | 8/2008 |
| WO | 2018064578 A1 | 4/2018 |

OTHER PUBLICATIONS

European Patent Office, Extended European Search Report, Application No. 21759691.5, Mar. 7, 2024, 8 pages.

(Continued)

*Primary Examiner* — Javier G Blanco
(74) *Attorney, Agent, or Firm* — Polsinelli PC

(57) ABSTRACT

An intraocular drug delivery platform including a ring having an anterior surface and a posterior surface opposite the anterior surface, a central aperture formed by the ring, a first haptic coupled to and extending outwards from the ring, a second haptic coupled to and extending outwards from the ring, a first drug eluting mass operably coupled to the anterior surface of the ring, and a second drug eluting mass operably coupled to the anterior surface of the ring and positioned directly opposite of the first drug eluting mass.

11 Claims, 3 Drawing Sheets

Related U.S. Application Data

(60) Provisional application No. 62/980,620, filed on Feb. 24, 2020.

(52) U.S. Cl.
CPC ............... *A61F 2002/16902* (2015.04); *A61F 2220/0025* (2013.01); *A61F 2250/0068* (2013.01)

(56) References Cited

U.S. PATENT DOCUMENTS

| | | | |
|---|---|---|---|
| 2011/0040378 A1* | 2/2011 | Werblin | A61F 2/1648 623/6.34 |
| 2011/0313521 A1* | 12/2011 | Angelopoulos | A61F 2/1694 623/6.43 |
| 2015/0100046 A1 | 4/2015 | Ambati et al. | |
| 2015/0342725 A1 | 12/2015 | Cuevas et al. | |
| 2016/0256262 A1 | 9/2016 | Wortz et al. | |
| 2017/0119521 A1 | 5/2017 | Kahook et al. | |
| 2021/0267751 A1 | 9/2021 | Sussman et al. | |

OTHER PUBLICATIONS

Patent Cooperation Treaty, International Search Report and Written Opinion, International Application No. PCT/US2021/019404, mailed Jun. 10, 2021, 11 pages.

* cited by examiner

INTRAOCULAR DRUG DELIVERY PLATFORM

CROSS-REFERENCE

This application is a continuation U.S. patent application Ser. No. 17/183,985, filed Feb. 24, 2021, which claims the benefit of U.S. Provisional Application No. 62/980,620, filed Feb. 24, 2020, which applications are incorporated herein by reference in their entireties for all purposes.

FIELD OF THE INVENTIONS

The inventions described below relate to the field of intraocular drug delivery platforms.

BACKGROUND

Intraocular lenses may be used in conjunction with drug delivery devices. In previous applications, such as U.S. application Ser. No. 16/516,356, filed Jul. 19, 2019, we disclosed various modular embodiments of intraocular lenses (IOL's) and drug delivery devices disposed in various ways to the intraocular lenses. The devices and methods described below provide for more convenient means of adding a drug delivery platform to a modular IOL and drug delivery platform.

SUMMARY

The devices and methods described below provide for placement of a drug delivery platform, in conjunction with an IOL, in a configuration that limits or prevents relative movement of the IOL and drug delivery platform and allows for replacement of a drug eluting mass which is disposed in a compartment of the drug delivery platform. The drug delivery platform comprises a ring, with a compartment or compartments or other means for releasably holding drug eluting mass or other solid drug mass (which may erode or slowly disintegrate or dissolve with the eye) on the anterior side of the ring. The drug delivery platform also includes a skirt extending posteriorly from the posterior surface. The skirt circumscribes, partially or fully, the aperture, and is configured with an inner diameter sized to retain the IOL lens within the wall of the skirt, or between segments of skirt. The inner diameter of the skirt is preferably larger than the intraocular lens of the intraocular lens assembly and the aperture. The skirt is configured to extend around the intraocular lens to prevent the platform from migrating to, or toward, the visual axis and blocking the patients field of view. The skirt is configured to constrain movement, including lateral or inferior/superior movement, of the intraocular lens relative to the ring.

DETAILED DESCRIPTION OF THE INVENTIONS

Figure 1:
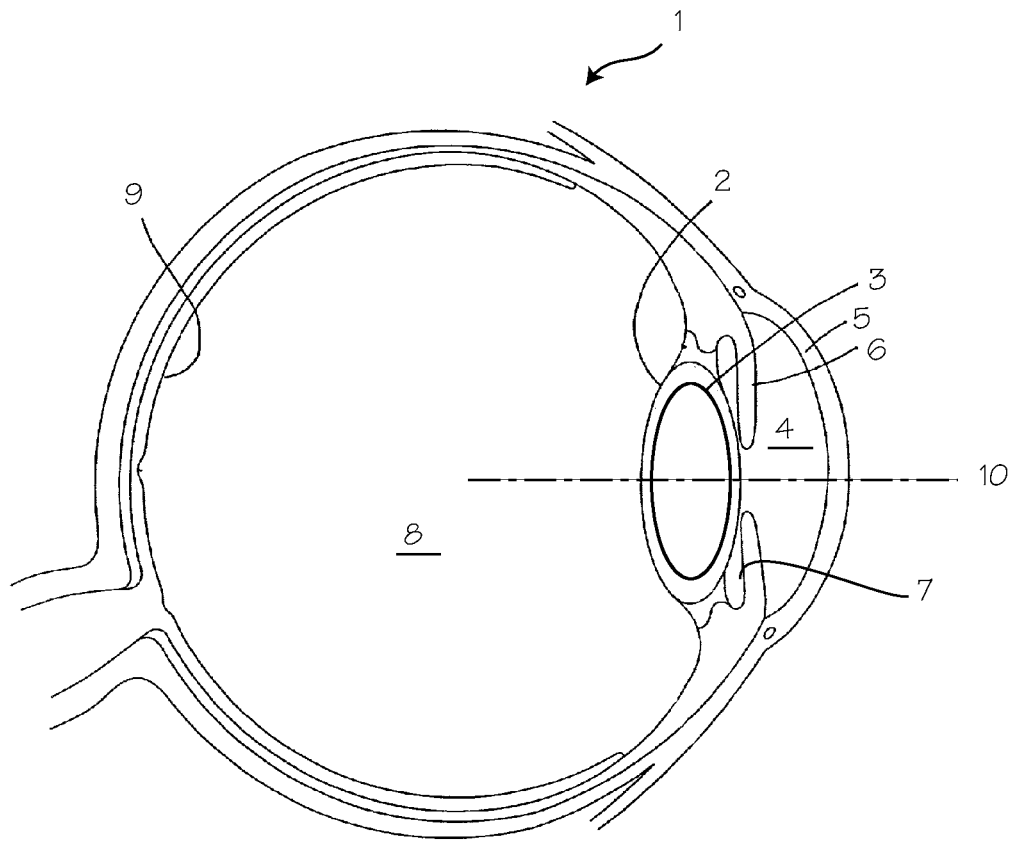
FIGS. 1 and 2 illustrate the environment of use of an intraocular drug delivery system.
Figure 2:
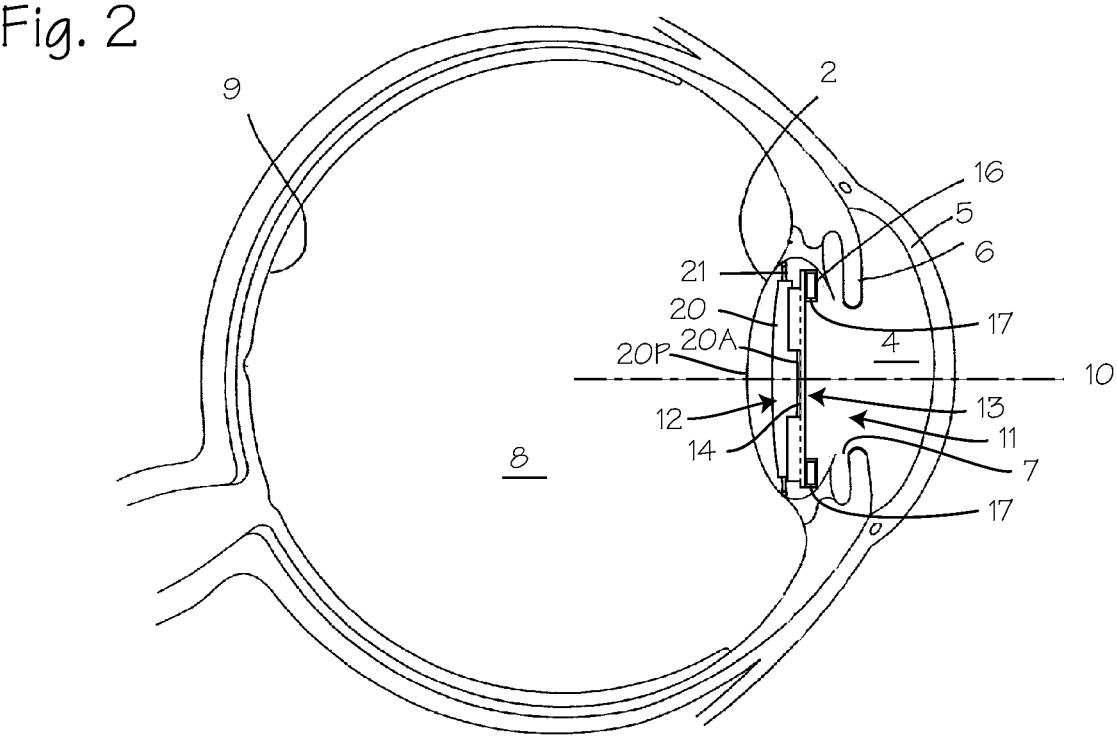

FIGS. 1 and 2 illustrate placement and use of an intraocular drug delivery system in the eye of a patient. The eye 1 includes a lens 2 (the natural lens of the eye) and lens capsular bag 3, and the anterior chamber 4 which includes the cornea 5 and iris 6 and aqueous humour filling the space between the cornea and the iris, and the ciliary sulcus (the posterior chamber) 7 between the iris and the capsular bag. The posterior cavity/vitreous body 8 is the large space between the lens and the retina 9. The natural lens 2 of the eye is characterized by an optical axis 10. (In the following description of the drug delivery platform and associated intraocular lens assembly, the terms posterior and anterior will be used in relation to the anatomy of the eye, in which the cornea is anterior and the retina is posterior.)

FIG. 2 illustrates a placement of the drug delivery platform 11 in the eye, along with an intraocular lens assembly 12. In this example, the drug delivery platform 11 is provided in the form of a ring and is implanted in the capsular bag in conjunction with an intraocular lens assembly 12. As shown in FIG. 2, the drug delivery platform can be installed alone, but is intended for use with the intraocular lens assembly 12. As shown in FIG. 2, the drug delivery platform is disposed anteriorly to (in front of) the intraocular lens assembly 12, and is fitted over the intraocular lens with a retaining rim or skirt extending posteriorly (behind) (relative to the anatomy of the eye). The drug delivery platform may also be placed below the iris and above the capsular bag. The capsular bag may contain the native lens, an artificial lens or no lens at all.

Figure 3:
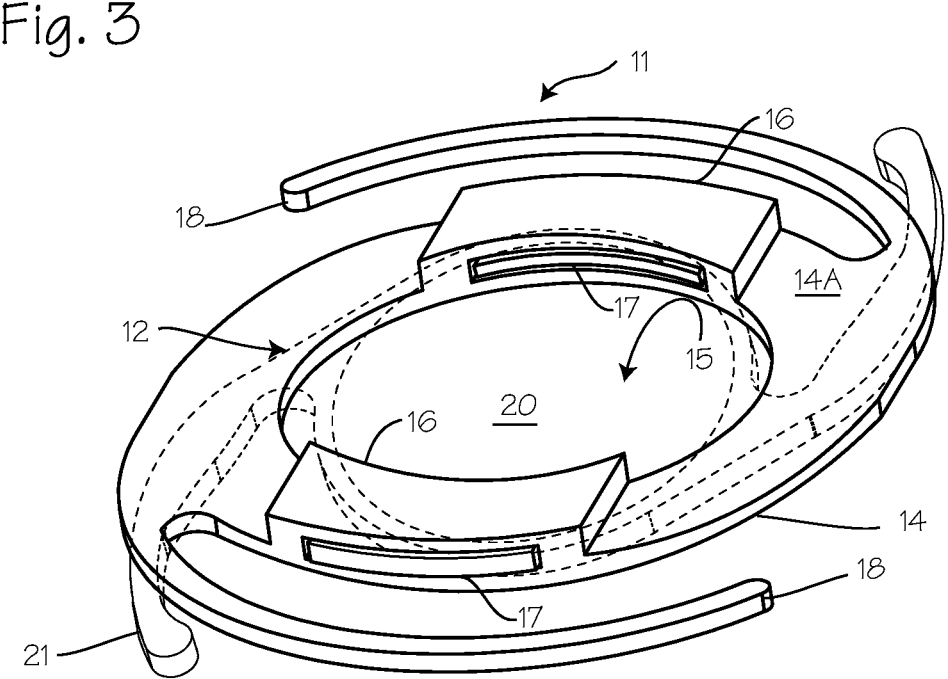
FIG. 3 illustrates the drug delivery platform configured for use in conjunction with an intraocular lens assembly.

FIG. 3 is an anterior view of the drug delivery platform of FIG. 2 configured for use in conjunction with an intraocular lens assembly. The drug delivery platform comprises a ring 14, which is preferably flat like a washer, and preferably a complete ring, without gaps, continuous along the entire 360° circumference of the ring, with an anterior surface 14A and a posterior surface 14P (shown in FIG. 4) and a central aperture 15. On the anterior surface, the drug delivery platform includes one or more compartments 16 configured to hold drug eluting masses 17. A single compartment may be provided, without more, but it may be preferred to provide two or more compartments disposed about the ring. The drug eluting masses may be provided in the form of blocks, slabs, wafers, cylindrical or spherical pellets configured to fit securely in a compartment with an interior space with a shape which accommodates the mass.

The masses may be inserted in the compartments before implantation or after implantation. The compartments are configured, relative to the masses, to hold the masses in a friction fit or other releasable attachment means, so that the masses can be inserted, removed and replaced while the platform remains in the eye using tools inserted through the cornea or a slit made between the cornea and the sclera. The compartments have an open side, as shown, which may be on the inside edge of the ring or outside edge of the ring, or a radial edge to allow insertion and removal of the masses. The compartments provide a convenient means for releasably securing the masses to the ring, such that the masses may be readily installed and removed and/or replaced without the use of special tools beyond simple graspers or hooks. Other releasable attachment means may be employed to secure the masses or other replaceable drug matrices to the drug delivery platform 11, such as snap ring fittings comprising annular matrices and corresponding annular detents on the drug delivery platform, or snap-fitting detents within recesses on the ring coupled with corresponding detent receiving recesses on the masses.

The drug delivery platform may also include haptics 18, which are outwardly biased filaments configured to impinge on the inside equator of the lens capsular bag 3 (where the drug delivery platform is to be implanted in the capsular bag) and hold the ring centrally within the lens capsular bag 3 and aligned with the optical axis of the eye.

Figure 4:
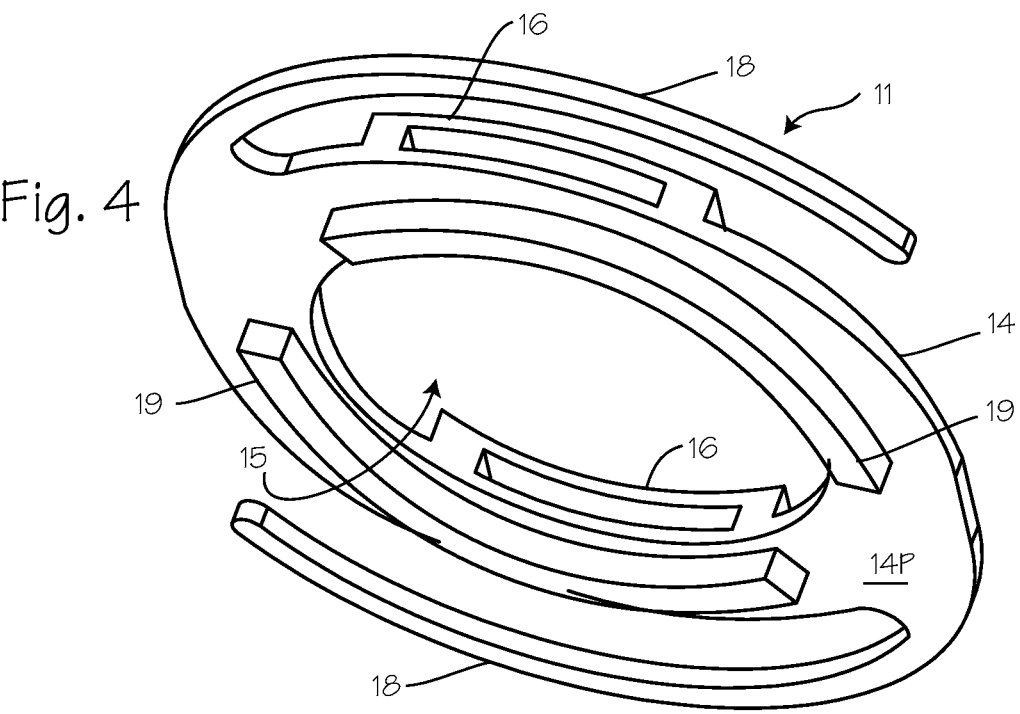
FIG. 4 is a posterior view the drug delivery platform of FIG. 3.

FIG. 4 is a posterior view of the drug delivery platform of FIG. 3. This view shows the posterior surface 14P of the ring 14, the central aperture 15, and the platform haptics 18. An intraocular lens retaining structure, such as an annular skirt 19 extends posteriorly from the posterior surface 14P and circumscribing, partially or fully, the aperture. The skirt is configured to prevent the drug delivery platform from migrating into the optical zone of the intraocular lens with which it is used (or, correspondingly, to retain the lens component of an intraocular lens assembly within the skirt). The skirt need not extend fully 360° around the aperture and may be interrupted by gaps, or, the skirt may be provided in several skirt segments with each segment partially circumscribing the aperture, so long as the segments are disposed about the aperture to fix the ring over the lens relative to the plane of the lens, the ring or the combined assembly of the ring and lens. The skirt defines a secondary aperture, with an inner diameter slightly larger than the aperture and the intraocular lens, such that the lens may fit within the skirt, while the aperture of the ring is slightly smaller than the lens, so as to prevent or limit movement of the lens to a position anterior to the ring. The inner diameter of the skirt secondary aperture may be configured to allow some slight lateral and/or superior/inferior movement of the lens within the skirt.

Figure 5:
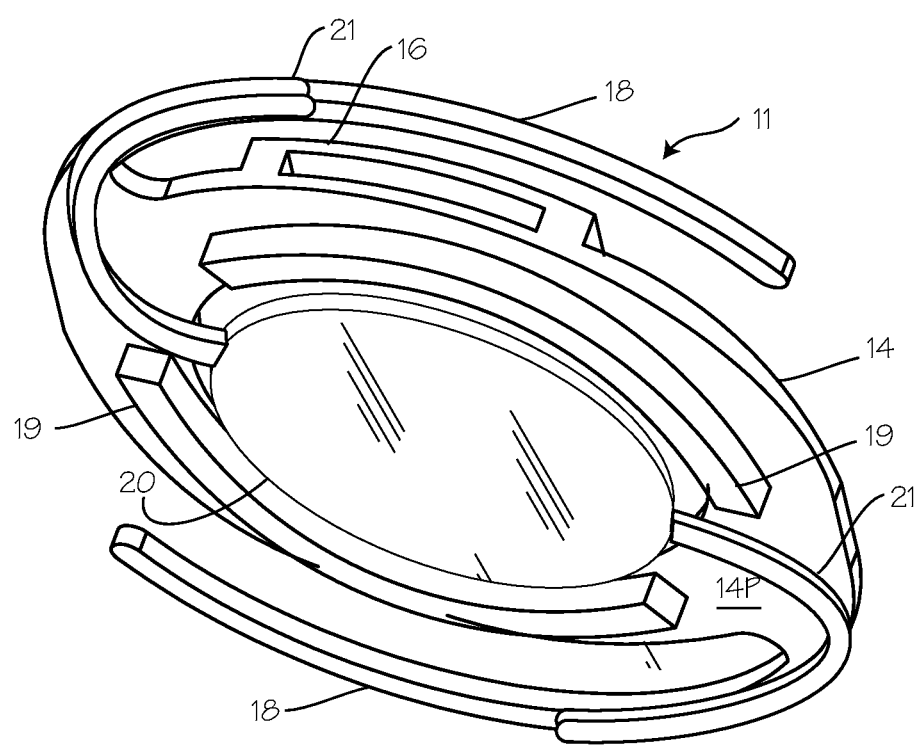
FIG. 5 is a posterior view of the combined drug delivery platform and intraocular lens assembly.

FIG. 5 is a posterior view of the combined drug delivery platform and intraocular lens assembly 12, as they would be arranged upon implantation in the eye. The intraocular lens assembly includes the intraocular lens 20 itself and, typically, a pair of lens haptics 21. The lens haptics, like the platform haptics, are outwardly biased filaments configured to impinge on the inside equator of the lens capsule to hold the lens centrally within the lens capsule and aligned with the optical axis of the eye. As shown in FIG. 5, the lens 20 is constrained within the inner boundaries of the skirts, and thus aligned along a common posterior/anterior axis with the ring 14 of the platform 13. While the lens may be somewhat free to move posteriorly/anteriorly relative to the ring, the haptics will function to maintain both components in parallel planes close to the equatorial plane of the lens capsular bag 3, or in co-planar relationship, with both preferably centered on the optical axis 10 of the eye when implanted in the capsular bag.

The masses 17 are sized and dimensioned to be inserted into the compartments, and retained in the compartments through a friction fit. The masses may comprise a matrix infused or impregnated with a therapeutic agent. Suitable matrix material includes silicone, hydrogel, PLGA, PVA, PLA, bio-erodible or biodegradable polymers, non-degradable medical grade polymers, or other polymer or non-polymer diffusion barriers. Suitable therapeutic agents include bimatoprost and other prostaglandin analogs, beta blockers, alpha agonists, carbonic anhydrase inhibitors, and rho kinase inhibitors. Crystalline forms of bimatoprost embedded in silicone are currently preferred for long term treatment of glaucoma. Other therapeutic agents can be used for long term treatment of macular degeneration, vasculopathies, corneal dystrophies, corneal degeneration, genetic pathologies, myopia, refractive abnormalities, presbyopia, uveitis, edema, post-operative inflammation, or other ocular or periocular diseases.

The masses 17 are preferably sized and dimensioned to be inserted into the compartments, and retained in the compartments through a friction fit (or any other suitable releasable attachment arrangement). The masses, the compartment, or both may include a semi-permeable membrane to control diffusion or elution of the therapeutic agent from the mass. Also, the compartment may be perforated with apertures sized to control the exposure of the mass to surrounding tissue, and thus control the rate of elution of therapeutic agent from the mass.

In use, the drug delivery platform may be used in a method for intraocular delivery of therapeutic agent into an eye of a patient, after implantation of an intraocular lens or along with the implantation of an intraocular lens. A surgeon will insert the intraocular drug delivery platform (13) described above into the eye of the patient and place the intraocular drug delivery platform (13) in a position anterior to (in front of) the intraocular lens also disposed within the eye of the patient such that the posterior surface of the ring is opposed to an anterior surface of the intraocular lens, and such that the intraocular lens is disposed within the skirt. (The surgeon may instead place the intraocular drug delivery platform (13) in a position posterior to the intraocular lens assembly, in which case the intraocular drug delivery platform (13) may be fabricated with the skirts extending anteriorly from the anterior surface 14A of the ring, such that an anterior surface of the ring is opposed to a posterior surface of the intraocular lens, and such that the intraocular lens is disposed within the skirt). If the drug delivery platform is initially provided with the compartments empty, and inserted into the eye with the compartments empty, then, after the intraocular drug delivery platform is disposed within the eye of the patient, the surgeon will insert a first drug eluting mass into the eye of the patient and secure the first drug eluting mass to the ring with the releasable attachment means. Where the releasable attachment means comprises the compartment (16) disposed on the anterior surface, and the compartment has an opening for receiving and/or removing the mass from the compartment, the surgeon will insert the first drug eluting mass (which is sized and dimensioned for a friction fit within the compartment) and securing the first drug eluting mass to the ring by inserting the first drug eluting mass into the compartment. Thereafter, the surgeon may remove the first drug eluting mass from the ring and secure a second drug eluting mass to the ring, while the drug delivery platform remains in the eye of the patient. The surgeon can replace a mass when it is exhausted, having eluted most or all of its therapeutic agent, or replace a mass with a second mass containing a second therapeutic agent different from the first therapeutic agent in the first mass. (Where the masses are biodegradable, upon complete degradation or erosion the surgeon may simple insert new masses).

If the drug delivery platform is initially provided with the compartments holding drug eluting masses, and inserted into the eye with the compartments filled with a first mass (or first masses), then, after the intraocular drug delivery platform is disposed within the eye of the patient, the surgeon will leave the drug delivery platform and masses in the eye for an extended period. Upon exhaustion of the masses, the surgeon may remove the first drug eluting mass from the ring and secure a second drug eluting mass to the ring, while the drug delivery platform remains in the eye of the patient. The surgeon can replace a first mass when it is exhausted, having eluted most or all of its therapeutic agent, or replace a mass with a second mass containing a second therapeutic agent different from the first therapeutic agent in the first mass. (Where the masses are biodegradable, upon complete degradation or erosion the surgeon may simple insert new masses). Where the releasable attachment means comprises the compartment (16) disposed on the anterior surface, and the compartment has an opening for receiving and/or removing the mass from the compartment, the surgeon will insert the second drug eluting mass (which is sized and dimensioned for a friction fit within the compartment) and secure the second drug eluting mass to the ring by inserting the second drug eluting mass into the compartment.

The advantages of the releasable attachment means may be achieved with or without the advantages of the lens retaining structure, and the advantages of the lens retaining structure may be achieved with or without the advantages of the releasable attachment means. For example, for phakic patients (patients with an intact natural lens), the drug delivery platform may be provided without the lens retaining skirt. The drug delivery platform may be implanted in the ciliary sulcus, with the platform haptics engaging the ciliary sulcus anterior to the (intact) capsular bag. For pseudophakic patients (patients with a previously implanted intraocular lens) the drug delivery platform may be implanted in the ciliary sulcus, with the platform haptics engaging the ciliary sulcus anterior to the (intact) capsular bag. In an embodiment of the method of implanting the device for phakic and pseudophakic patients in the ciliary sulcus, the drug delivery platform may be provided with haptics configured to impinge on the outer perimeter of the ciliary sulcus. For aphakic patients (patients with no lens at all), the drug delivery platform may be provided with haptics configured to impinge on the outer perimeter of the ciliary sulcus, or it may be provide with haptics configured to impinge the capsular bag, and may be implanted at the corresponding location, and may be provided with or without the skirt.

The drug delivery platform itself, including the ring alone, the skirt alone, or both the ring and the skirt, may comprise a drug eluting mass or other solid drug mass (which may erode or slowly disintegrate or dissolve with the eye), and may be configured without a separate drug eluting mass (17). In this configuration, the drug delivery platform comprised all the features of the drug delivery platform of FIGS. 3 and 4, including the ring 14 with the anterior surface 14A and posterior surface 14P and the central aperture 15, and, optionally, the compartments 16 configured to hold drug eluting masses 17, the platform haptics 18, and the annular skirt 19 extending posteriorly from the posterior surface 14P and circumscribing, partially or fully, the aperture. The compartment 17 may be emitted, or retained for use with a drug eluting mass containing a therapeutic agent. The platform may include a first therapeutic agent, and the drug eluting mass in the compartment can include a second therapeutic agent different from the first therapeutic agent.

The advantages of the lens retaining structure may be obtained without the benefits of the releasable attachment means. For example, a method for intraocular delivery of an IOL into a patient can include the steps of inserting a ring (14) having an anterior surface (14A) and a posterior surface (14P) and a central aperture (15), a skirt (19) extending posteriorly from the posterior surface (14P), said skirt circumscribing, partially or fully, the aperture (15) where the skirt (19) is configured to retain the intraocular lens assembly (12), with an inner diameter larger than both an intraocular lens (20) of the intraocular lens assembly and the aperture (15). The ring may be configured as a centering device for the IOL or as a carrier for a pinhole device or a second lens to correct astigmatism, refractive error or to multifocality.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

What is claimed is:

1. An intraocular implant comprising:
   an intraocular drug delivery platform comprising:
   at least a partial ring comprising an anterior surface, a posterior surface opposite the anterior surface, and a central aperture formed by the ring;
   at least one discrete compartment comprising a first discrete compartment extending anteriorly from the anterior surface of the ring and integrated with the ring;
   a first drug eluting mass comprising a therapeutic agent positioned in the first discrete compartment;
   a retention structure extending posteriorly from the posterior surface of the at least a partial ring and at least partially circumscribing the central aperture; and
   an intraocular lens (IOL) configured to be retained in position by the retention structure of the intraocular drug delivery platform, the IOL comprising an optic, a first lens haptic, and a second lens haptic.

2. The intraocular implant of claim 1, wherein the first drug eluting mass is in the form of a slab.

3. The intraocular implant of claim 1, wherein the retention structure comprises a skirt.

4. The intraocular implant of claim 1, wherein the first drug eluting mass includes a membrane to control a rate of elution of the therapeutic agent.

5. The intraocular implant of claim 4, wherein the membrane is a semi-permeable membrane.

6. The intraocular implant of claim 1, wherein the therapeutic agent of the first drug eluting mass is dispersed within a first matrix of the first drug eluting mass.

7. The intraocular implant of claim 6, wherein the first matrix is a silicone matrix.

8. The intraocular implant of claim 1, wherein the therapeutic agent comprises bimatoprost.

9. The intraocular implant of claim 8, wherein the bimatoprost is in a crystalline form.

10. The intraocular implant of claim 1, wherein the at least one discrete compartment further comprises a second compartment, and a second drug eluting mass being positionable in the second compartment.

11. The intraocular implant of claim 10, wherein the second compartment extends anteriorly from the anterior surface of the ring.

* * * * *